United States Patent [19]

Poler

[11] 4,270,230
[45] Jun. 2, 1981

[54] INTRAOCULAR LENS

[75] Inventor: Stanley Poler, New York, N.Y.

[73] Assignee: Lynell Medical Technology Inc., New York, N.Y.

[21] Appl. No.: 100,243

[22] Filed: Dec. 4, 1979

[51] Int. Cl.³ .............................. A61F 1/16; A61F 1/24
[52] U.S. Cl. ............................................................ 3/13
[58] Field of Search ........................................... 3/13, 1

[56] References Cited

U.S. PATENT DOCUMENTS

| | | | |
|---|---|---|---|
| 3,925,825 | 12/1975 | Richards et al. | 3/13 |
| 4,080,709 | 3/1978 | Poler | 3/13 X |
| 4,110,848 | 9/1978 | Jensen | 3/13 |
| 4,122,556 | 10/1978 | Poler | 3/13 |
| 4,159,546 | 7/1979 | Shearing | 3/13 |
| 4,174,543 | 11/1979 | Kelman | 3/13 |

Primary Examiner—Ronald L. Frinks
Attorney, Agent, or Firm—Hopgood, Calimafde, Kalil, Blaustein & Judlowe

[57] ABSTRACT

The invention contemplates improved intraocular-lens structures for use as implants in ophthalmological surgery, the lens being a replacement for a cataract-clouded natural lens, and the replacement being installed in the pupil at the iris as the operative step following removal of the cataracted lens. The lens features adapter structure assembled to an optically finished lens element and including one or more stabilizing feet which are formed integrally with the body of the adapter and which are axially offset from the adapter body to permit the stabilizing feet and the adapter body to engage opposite sides of the iris.

29 Claims, 11 Drawing Figures

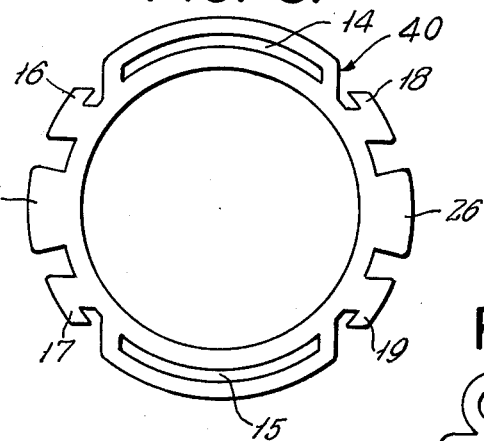
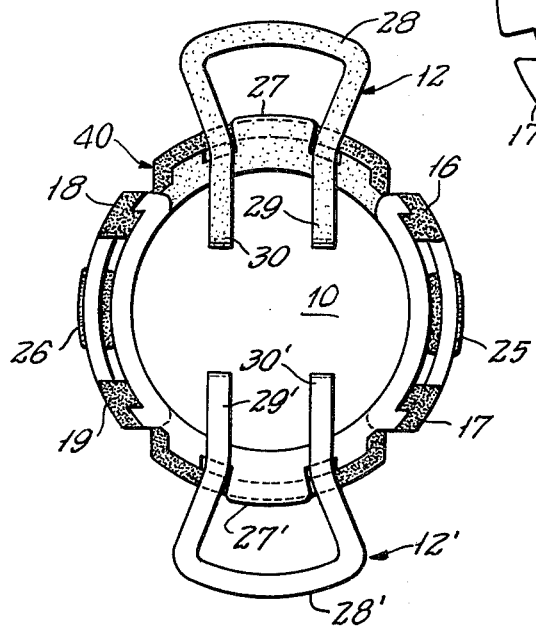
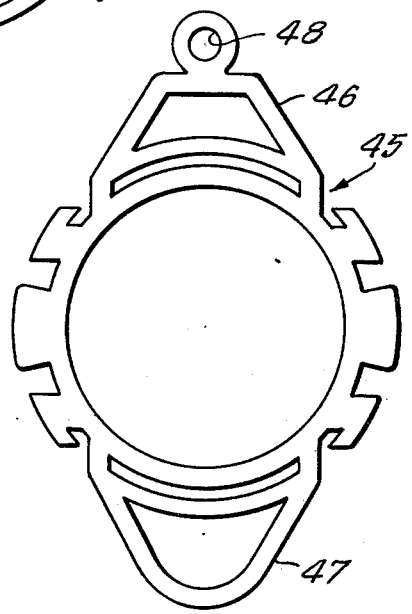
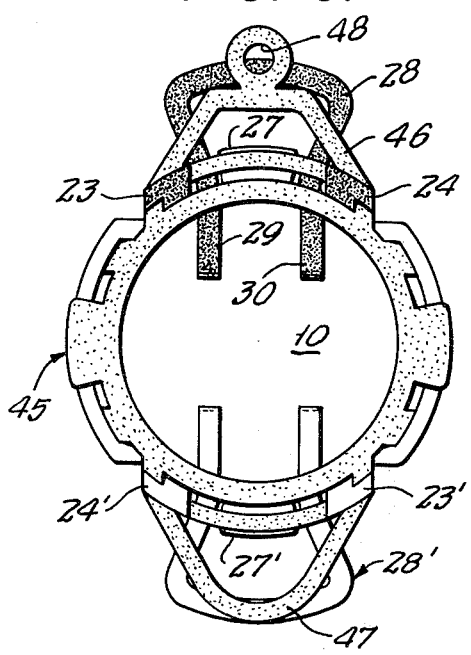
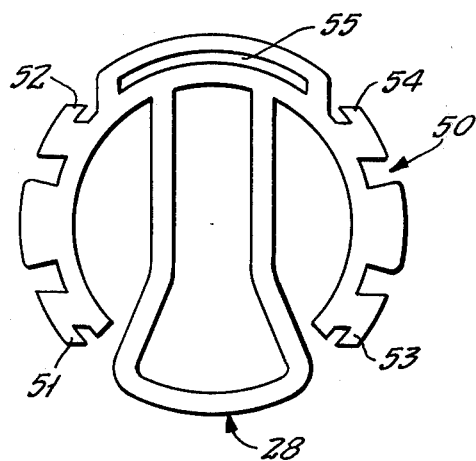

INTRAOCULAR LENS

BACKGROUND OF THE INVENTION

This invention relates to structures for making an improved lens implant, as a replacement for a cataract-clouded or otherwise diseased natural lens. The invention represents improvement over structures described in my U.S. Pat. No. 4,122,556 and in my copending application, Ser. No. 57,323, filed July 13, 1979, and over my various other patent disclosures referred to in said patent and application. Reference is therefore made to said patent and application and disclosures for greater background detail as to structure, and manufacturing and manipulating technique.

Regardless of the structure of an intraocular lens and its mount, relatively great skill is required for installation at or through an iris opening, if post-operative trauma are to be avoided. The likelihood of such trauma is also reduced, to the extent that lens mounting structure imposes least restriction upon normal aperture responses of the iris.

BRIEF STATEMENT OF THE INVENTION

It is an object of the invention to provide improved mounting structure for an intraocular lens.

Another object is to provide such structure lending itself to simplified installation at or via the iris.

It is a specific object to provide such structure with trans-iris stabilizing means placing substantially zero restriction upon iris action, as compared with prior constructions.

Another specific object is to meet the preceding object with haptic structure which can derive at least a significant component of lens-stabilizing support from the posterior-chamber wall, for the case of anterior-chamber positioning of an implanted lens.

It is also a specific object to provide such structure which lends itself to posterior implantation in a human eye and which is inherently resistive against such secondary membrane growth (i.e., corpuscular regrowth) as might otherwise obscure or degrade optical performance of the implanted lens.

Still another specific object is to achieve the above objects with structure which is inherently capable of securely and accurately positioning an optically finished glass lens element.

A further specific object of the invention is to provide three-piece lens-adapter structure which is modular to the extent that it is inherently adaptable with little or no modification to one or more different modes of support within the eye, such modes being selectable at the surgeon's option.

The foregoing and other objects and features of the invention are achieved in an illustrative series of embodiments by providing annular adapter structure which axially retains itself against both axial sides of the peripheral rim of the lens element to which it is assembled. The adapter structure comprises an annular body member for engagement with one axial side of a lens element, and one or more arcuate body members are connected in registry with the annular body member for retaining engagement with the other axial side of the lens element. Plural stabilizing feet are provided as radially outward projections which have axially offset integral connection to the radially inner edge of the one or more arcuate bodies of the adapter.

In the forms to be described, the adapter body and its stabilizing feet are formed from compliant sheet material, the axial-offset and radially-projecting parts of the stabilizing feet being permanently bent to ultimate configuration, in a secondary operation. The ability to use the same adapter blank for production of lens-mounting structure wherein the axial offset of stabilizing feet can be at selected different radii about the axis of optical symmetry is significant, in that the structure of the invention can be simply completed to such radius of stabilizing-foot offset as a particular ophthalmological surgeon may prescribe for a particular patient, such radius being selectable, for example, within a 2:1 range of prescribed radii, for the case of an implanted optically finished glass lens of 5 mm diameter.

DESCRIPTION OF PREFERRED EMBODIMENTS

Preferred embodiments of the invention are shown in accompanying drawings, taken in conjunction with ensuing text. In said drawings:

FIG. 7 is a view similar to FIG. 1 to show a third embodiment;

FIG. 8 is a plan view of a mounting part used in the structure of FIG. 7;

FIGS. 9 and 10 are respectively similar to FIGS. 7 and 8, for the case of a fourth embodiment; and FIG. 11 is a blank outline of a modified haptic having analogous use in various of the foregoing combinations.

Figure 2:
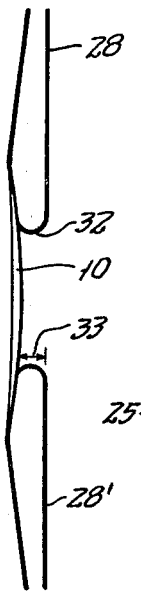
FIG. 2 is a side view of the construction of FIG. 1.
Figure 3:
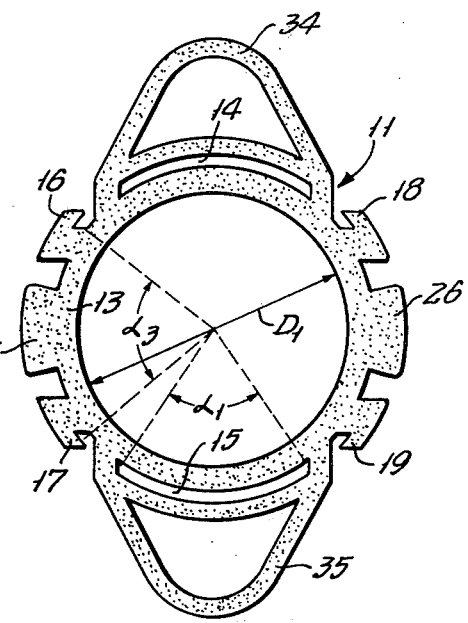
FIGS. 3 and 4 are blank outlines of mounting haptic parts employed in the structure of FIG. 1.
Figure 4:
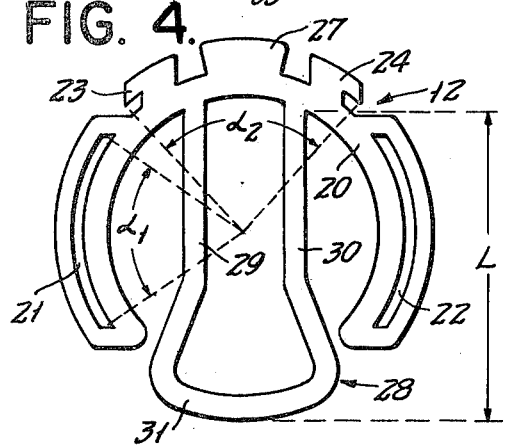

In FIGS. 1 to 4, the invention is shown in application to mounting haptic structure for a finished optical lens element 10 to be surgically implanted in a human eye, relying upon the iris for stabilized support of the implant. The mounting structure comprises three parts, a single annular body part 11 (FIG. 3), and two like arcuate body parts 12-12' (FIG. 4). Fully assembled, these parts circumferentially continuously overlap opposite axial sides of the rim or peripheral region of lens 10 and are connected to each other at angularly spaced locations adjacent the lens periphery.

The anterior side of the lens is supported by the annular body part 11, which is characterized by a circumferentially continuous body portion 13 having a circular inner edge of diameter $D_1$ less than the diameter $D_2$ of lens 10 and otherwise in radial overlap with the lens periphery. Each of the arcuate body members 12 (12') has an arcuate inner edge substantially meeting the corresponding dimensional relation stated above for the annular body member 11; these arcuate body members are of effectively three-quadrant angular extent, and they are assembled in equal one-quadrant overlap at their respective circumferential ends, to effectively circumferentially continuously lap the posterior side of the peripheral region of lens element 10.

For connected assembly of haptic parts 11-12-12' to each other and to lens element 10, the peripheral regions of all body portions are similarly formed with hook and slot formations such that, when assembled, they have diametrically opposite symmetry in diametrically opposite quadrants about the central optical axis. Thus, for the case of annular body member 11 and within a first pair of diametrically opposed quadrants, first and second diametrically symmetrical extensive arcuate slots 14-15 are formed in the annulus of body portion 13; these slots 14-15 are of angular extent $\alpha_1$ approaching but less than 90 degrees, and they are at greater diameter than the diameter $D_2$ of lens element 10. And within the remaining or second pair of diametrically opposed quadrants, first and second pairs of diametrically symmetrical hook formations 16-17 and 18-19 project in the circumferentially outward direction with respect to the involved quadrant.

In similar fashion, the diametrically opposed quadrants of the body portion 20 (20') of the respective arcuate body members 12 (12') are formed with first and second arcuate slots 21-22 of angular extent $\alpha_1$, and the remaining or intermediate quadrant of body portion 20 includes first and second pairs of hook formations 23-24 which project in the circumferentially outward direction with respect to the involved quadrant.

The slot formations 21-22 of one (12) of the arcuate body members are designed for angularly registered overlap when the body members 12-12' are assembled with their intermediate quadrants in diametric opposition. And the hook formations 16-17 (18-19) of annular body member are designed for interlocked engagement in the respectively registering pairs of arcuate slots 21-22 in the thus-overlapped arcuate body members 12-12', while the hook formations 23-24 of arcuate body member 12 have interlocked engagement in the arcuate slot formation 14, and the corresponding hook formations 23'-24' of the other arcuate body member 12' have interlocked engagement in the arcuate slot formation 15. To this end, the hook ends in a given quadrant (of either of the body shapes 11-12) are at an angular spread $\alpha_2$ which exceeds the effective slot width $\alpha_1$, and the closed end of the hook openings in a given quadrant are at an angular spread $\alpha_3$ which is less than the effective slot width $\alpha_1$. And tabs 25-26-27-27' between the respective pairs of hook formations 16-17, 18-19, and 23-24 will be understood to assist in stabilizing all hook and slot engagements.

In accordance with a feature of the invention, the inner almost-circular region of each arcuate body member, such as member 12, has integrally formed structure which after permanent bending in a secondary operation, defines a foot or haptic 28 for ultimate engagement with the posterior side of the iris and for radially compliant referencing contact with the adjacent region of the wall of the posterior chamber of the eye. Prior to secondary operations, foot 28 is of length L substantially exceeding the inner-edge diameter $D_1$, being shown to comprise two parallel legs 29-30 which are integral with the inner arcuate edge of body 20 and which are symmetrically positioned (at an overall spacing $S_1$) in the intermediate quadrant of body 20. Legs 29-30 diverge at their outer ends, where they are integrally connected by an arcuate bow 31, which is relied upon for wall contact in the posterior chamber.

In the secondary operation, legs 29-30 are folded to substantially the shape depicted at 32 in FIG. 2, thereby establishing a rearward offset 33 in the reversed orientation of the posterior-contact end 31 of foot 28. The location and axial extent 33 of the bend 32 is a matter for the surgeon's prescription, but it is generally preferred that this bend be so selected that when both arcuate body members 12-12' are assembled, their corresponding inner-bend limits are spaced by a span $S_2$ which is designed for trans-iris placement, with substantially zero contact at the iris opening, under the most contracted conditions. I find that with $S_1$ and $S_2$ both equal to 2 mm, and with an axial offset 33 of about half a millimeter, there is virtually no interference with iris-dilating and constricting reaction to normally encountered changes in ambient illumination brightness.

Figure 1:
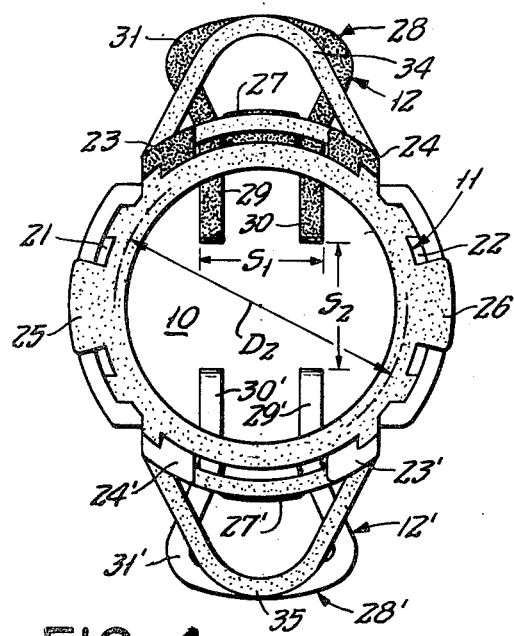
FIG. 1 is a view in front elevation of an intraocular lens of the invention, complete with assembled mounting structure.

To complete the description of FIGS. 1 to 3, the annular body member is shown to be integrally formed with additional relatively stiff radially outward foot formations 34-35 at diametrically opposite locations. These foot formations are generally arched and are rooted to body 13 at the ends of slots 14-15, and they are designed for stabilizing contact with the anterior side of the iris and, in certain cases, with the adjacent wall of the anterior chamber. Generally speaking, the overall span between tips of feet 34-35 is at least no greater than substantially 10 mm, being preferably in the range of 6 to 9 mm.

The fully assembled structure in FIG. 1 is seen to involve eight angularly spaced hook-to-slot interlocking engagements around the rim of lens element 10, with the radial stiff and axially compliant feet 34-35 projecting on a diametrical alignment of symmetry for anterior engagement with the iris, and with the axially and radially compliant feet 28-28' projecting on the same diametrical alignment for the indicated posterior engagements. The hook and slot patterns of the respective parts 11-12-12' are at 90-degree offset with respect to each other, to enable the described interlocking relation. And the lens element 10 is positively retained by and between circumferentially continuous body surfaces 13 and 20-20', with concentric mounting assured by the eight interlocking engagements. Finally, the short outward integral tab formations 25-26-27-27', between adjacent hook formations, radially overlap central regions of outer structure spanning the slots 14-15-21-22 to provide additional mutuality of body-member support.

Figure 5:
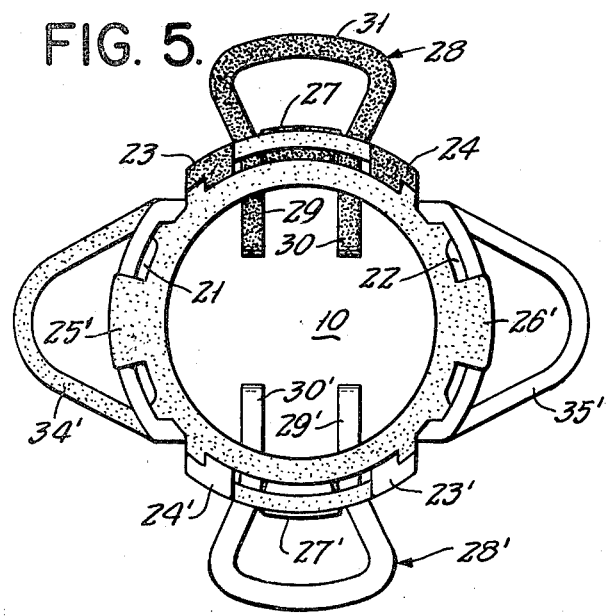
FIG. 5 is a view similar to FIG. 1 to show another embodiment.
Figure 6:
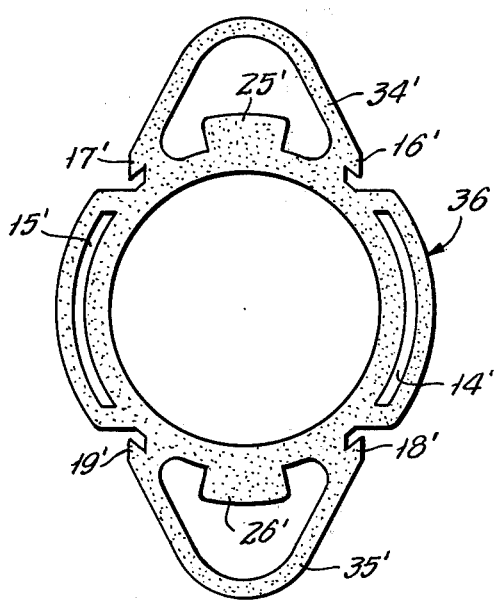
FIG. 6 is a view similar to FIG. 4 to show the mounting part which replaces that of FIG. 4 to make the embodiment of FIG. 5.

The embodiment of FIG. 5 is like that which has been described for FIG. 1, except that the different annular body member 36 of FIG. 6 is employed in place of the body member 11 of FIG. 3. In FIG. 6, body member 35 is seen to have integral bowed foot formations 34'-35' at the opposed quadrants which are characterized by hook formations 16-17 and 18-19, respectively, and the slotted regions 14'-15' are in the quadrants between foot formations 34'-35'. Angular criteria $\alpha_1$, $\alpha_2$, $\alpha_3$ for hook-and-slot engagements remain as previously described. The resultant assembly (FIG. 5) may be briefly described as a four-loop cross, in that the opposed feet 28-28' are at angular interlace with the opposed feet 34'-35'.

The embodiment of FIG. 7 is like those which have already been described, except that the annular body member 40 of FIG. 8 has been assembled to the two arcuate body members 12-12' in the manner already described; and FIG. 7 has been drawn from the posterior aspect, for a better showing of the overlapped relation of arcuate body members 12-12'. Body member 40 has no stabilizing legs or feet and serves to facilitate use of the Binkhorst technique in an irido-capsular implantation, wherein the contact feet 28-28' are implanted in and compliantly engage the inner surface of an excavated natural-lens capsule, the compliance being relied upon to automatically displace the lens 10 from the anterior chamber to the posterior chamber via a dilated iris, once anchoring-membrane growth has sufficiently secured the feet 28-28'.

The embodiment of FIG. 9 is in all respects like that of FIG. 1, except that the annular body member 45 of FIG. 10 has been assembled (in place of body member 11) to the two arcuate body members 12-12'. One (46) of the foot formations 46-47 of FIG. 10 incorporates a small aperture 48 at its outer end, to serve the optional preference of surgeons who elect to additionally rely on suture connection to the iris, at 48, or, alternatively, in an iridectomy, to depress the tab of aperture 48 through a surgical aperture in the iris and into retaining engagement behind the outer arc of foot 28 in the posterior chamber. For this purpose, it will be seen that the tab for aperture 48 extends into at least full radial overlap with the arcuate end of foot 28 and that this tab is integrally connected to the remainder of foot 46 at substantially the inner radius of the arcuate end of foot 28.

The embodiment of FIG. 11 is concerned with an alternate, but not presently preferred arrangement of the slotted and hook-characterized quadrants of the arcuate body members. In the member 50 of FIG. 11, the hook formations 51-52 and 53-54 are in the circumferentially outer quadrants, and the slot formation 55 is in the central or intermediate quadrant. Upon assembly to a selected annular body member, the overlapped hooks 51-51 of two lapped diametrically opposed such members 50 will be understood to engage the annular body member via one of its slots (e.g., slot 14) while the other overlapped hooks 53-54 engage the annular body member via the other one of its slots (e.g., slot 15).

The described body-member configurations and assemblies will be seen to utilize basic three-part lens-mounting structure which is to an extent modular, in that a wide variety of different anterior and posterior suspensions can be provided, to suit the professional preference or decision of the surgeon; the use of arcuate body members 12 (12') enables provision of greater available leg length at 28 (28'), providing a greater range of specification for span $S_2$, for offset 33, and for radially compliant effective bent-leg length. Of course, the surgeon will have specified the lens properties appropriate to the ultimate axial location at which he intends to make his implant. In all cases, finish-ground optical quality glass is preferred at lenses 10, generally of 5 mm diameter and 0.3 mm thickness, although if tolerated by the body, preformed plastic lenses may be used.

Reference has been made to thin-sheet compliant flexible material for the described mounting structure. This represents my preference, and I indicate my further preference to employ a stable, strong, flexible polyimide, selected for commercial availability and autoclavability. The precise formation of described blank configurations is preferably achieved through photolithographic techniques which are described in one or more of the patent disclosures referred to in my said patent and application. With all forms, the flexible sheet material is suitably 0.002-inch thick.

The described structures will be seen to achieve all stated objects and to provide an improved product suited to particular needs, and especially adaptable to use of identical lithographically fabricated body blanks with different radii of trans-iris posterior-chamber support, as may be variously prescribed by the ophthalmological surgeon.

Throughout the specification, I have made reference to stabilizing feet, at 28 (28') and 34-35, for reasons of consistency with language in my said prior patents and disclosures. However, I note for the record that the word "haptic" is becoming more current in application to my extremely light-weight mounting structures, undoubtedly because of the extremely gentle compliant nature of their stabilizing engagement with the iris. This gentle action is particularly true for inward legs of foot structures 28-28' of the present case, wherein the extreme ends are cantilevered from the body structure 20 approximately twice the overall distance by which feet 34-35 extend from the body 13. This fact, coupled with the substantially reduced radius at which the haptics 28-28' traverse the iris opening, is expected to materially reduce the likelihood of trauma attributable to the implanted device per se.

While the invention has been described in detail for the preferred forms shown, it will be understood that modifications may be made without departing from the claimed invention. For example, the structure of FIG. 7 lends itself to alternative employment wherein the lens 10 and the connected haptic parts 12-12'-40 are all installed in the posterior chamber, but with feet 28-28' extending through the iris for compliant engagement with the iris in the anterior chamber.

What is claimed is:

1. As an article of manufacture, an optically finished intraocular lens element having a generally circular periphery about its optical axis, and a mounting adapter for said lens element, said adapter comprising at least one circumferentially continuous annular body member having a circular inner edge of diameter less than the diameter of said lens element, at least one arcuate body member of inner-edge diameter substantially matching that of said circumferentially continuous annular body member, said body members being adjacent opposite axial sides of the peripheral region of said lens element and being connected to each other within a geometrical annulus radially outside said lens element, and a plurality of angularly spaced lens-positioning feet including at least one foot formed integrally with the inner edge of said arcuate body member, said one foot extending radially outwardly of the periphery of said lens element and at axial offset from said lens element.

2. The article of claim 1, in which said one foot is of length exceeding said inner-edge diameter.

3. The article of claim 1, in which said one foot is integrally connected to said arcuate inner edge at the angularly central region thereof.

4. The article of claim 1, wherein said one foot comprises two legs integrally formed with said arcuate inner edge at angularly spaced locations along said arcuate inner edge, said legs being of length exceeding said inner-edge diameter and integrally connected at their remote ends.

5. The article of claim 1, wherein the number of said arcuate body members is two, being connected to said circumferentially continuous body member at angularly spaced locations.

6. The article of claim 5, in which said arcuate body members are at diametrically opposed locations and are circumferentially interconnected.

7. The article of claim 1, wherein said arcuate body member is of compliant sheet material, said one foot being permanently bent from the sheet material of said arcuate body member.

8. The article of claim 1, in which each body member is of compliant sheet material, and in which interlocking formations in the sheet material of both body members establish the connection of said body members at a plurality of angularly spaced locations.

9. The article of claim 8, in which for each body member said formations comprise corresponding slot formations within a first pair of diametrically opposed quadrants and corresponding hook formations within remaining quadrants, the interconnection of said body members involving the hook formations of one body member engaged to the other body member via the slot formations of said other body member.

10. The article of claim 9, in which the hook formations of said other body member are engaged to said one body member via the slot formations of said one body member.

11. The article of claim 8, in which said arcuate body member is one of two like arcuate body members interconnected with said annular body member at angularly spaced locations.

12. The article of claim 11, in which each of said arcuate body members is of substantially three-quadrant extent, said arcuate body members having substantially one-quadrant overlap at their respective circumferential ends.

13. The article of claim 12, in which said arcuate body members have registering slot formations at their overlapped circumferential ends, the hook formations of said annular body member being engaged to said arcuate body members via said overlapped slot formations.

14. The article of claim 1, in which plural lens-positioning feet formed integrally with the outer edge of said annular body member extend radially outwardly at angularly spaced locations which are angularly spaced from the location of said foot.

15. The article of claim 1, in which plural lens-positioning feet formed integrally with the outer edge of said annular body member extend radially outwardly, said foot being in angular register with one of said last-defined feet.

16. The article of claim 15, in which one of said last-defined lens-positioning feet has an aperture formed therein at substantially its radially outer limit for sutured reference to adjacent iris tissue.

17. As an article of manufacture, an optically finished intraocular lens element having a generally circular periphery about its optical axis, and a mounting adapter for said lens element, said adapter comprising at least one circumferentially continuous annular body member having a circular inner edge of diameter less than the diameter of said lens element, at least one arcuate body member of inner-edge diameter substantially matching that of said circumferentially continuous annular body member, said body members being adjacent opposite axial sides of the peripheral region of said lens element and being connected to each other within a geometrical annulus radially outside said lens element, and a plurality of angularly spaced lens-positioning feet extending radially outwardly of the periphery of said lens element and having radially compliant integral connection to one of said body members.

18. As an article of manufacture, an optically finished intraocular lens element having a generally circular periphery about its optical axis, and a mounting adapter for said lens element, said adapter comprising at least one circumferentially continuous annular body member having a circular inner edge of diameter less than the diameter of said lens element, two arcuate body members of inner-edge diameter substantially matching that of said circumferentially continuous body member, said annular body member being adjacent one axial side of the peripheral region of said lens element and said arcuate body members being adjacent the other axial side of the peripheral region of said lens element and being connected to said annular body member within a geometrical annulus radially outside said lens element, and angularly spaced lens-positioning feet extending radially outwardly of said lens element and integrally connected to one or more of said body members.

19. The article of claim 18, in which each of said arcuate body members is integrally formed with one of said feet.

20. The article of claim 18, in which said arcuate body members have interconnected circumferential ends.

21. The article of claim 18, in which said feet are formed integrally with the inner edges of said arcuate body members, each of said feet extending radially outwardly of the periphery of said lens element and at axial offset from said lens element.

22. The article of claim 21, in which further angularly spaced lens-positioning feet are formed integrally with the outer edge of said annular body member, said first-mentioned feet and said further feet being of corresponding pluralities and at registering angular locations.

23. The article of claim 21, in which further angularly spaced lens-positioning feet are formed integrally with the outer edge of said annular body member, said first-mentioned feet and said further feet being of corresponding pluralities and at angularly interlaced locations.

24. The article of claim 21, in which said annular body member is an annulus having no lens-positioning foot formations.

25. The article of claim 17, in which the integral connection of said feet to said arcuate body members is radially compliant.

26. The article of claim 25, in which the angularly spaced radially stiff lens-positioning feet are formed integrally with the outer edge of said annular body member.

27. The article of claim 17, in which said optical element is of glass and said body members are each of polyimide sheet material.

28. The article of claim 12, in which said arcuate body members have registering hook formations at their overlapped circumferential ends, the slot formations of said annular body member being engaged to said arcuate body members via said overlapped hook formations.

29. The article of claim 15, in which said foot and the registering one of said last-defined feet have interengageable outer-end formations at least one of which is adapted to be manipulated through a surgical aperture in the iris, as a step preliminary to manipulated engagement of said outer-end formations.

* * * * *